(12) United States Patent
Dvorak et al.

(10) Patent No.: US 8,865,680 B2
(45) Date of Patent: Oct. 21, 2014

(54) SURGICAL GEL SYSTEM

(71) Applicant: Hemcon Medical Technologies (IP) Limited, Sallynoggin (IE)

(72) Inventors: Radim Dvorak, Sallynoggin (IE); Radka Bartosovska, Sallynoggin (IE); Jitka Vankova, Sallynoggin (IE); Sam Kuhn, Sallynoggin (IE); Keith Real, Sallynoggin (IE); Jennifer M. Genco, Sallynoggin (IE); Jennifer Adams, Sallynoggin (IE)

(73) Assignee: Hemcon Medical Technologies (IP) Limited, Sallynoggin, County Dublin (IE)

( * ) Notice: Subject to any disclaimer, the term of this patent is extended or adjusted under 35 U.S.C. 154(b) by 0 days.

(21) Appl. No.: 13/690,529

(22) Filed: Nov. 30, 2012

(65) Prior Publication Data

US 2013/0165402 A1    Jun. 27, 2013

Related U.S. Application Data

(63) Continuation of application No. PCT/IE2011/000029, filed on Jun. 1, 2011.

(60) Provisional application No. 61/344,167, filed on Jun. 3, 2010.

(51) Int. Cl.
*A61L 26/00* (2006.01)

(52) U.S. Cl.
CPC ......... *A61L 26/0052* (2013.01); *A61L 26/0023* (2013.01); *A61L 2400/04* (2013.01); *A61L 26/0047* (2013.01); *A61L 26/009* (2013.01); *A61L 26/0066* (2013.01)
USPC .......................................................... 514/54

(58) Field of Classification Search
CPC ............ A61L 26/0023; A61L 26/0047; A61L 26/0052; A61L 2400/04; A61L 26/0066; C08L 5/06
USPC .......................................................... 514/54
See application file for complete search history.

(56) References Cited

U.S. PATENT DOCUMENTS

| | | | |
|---|---|---|---|
| 6,372,718 B2 * | 4/2002 | Santar et al. ..................... 514/25 |
| 2004/0106730 A1 | 6/2004 | Santar | |
| 2006/0008505 A1 | 1/2006 | Brandon | |

FOREIGN PATENT DOCUMENTS

GB    2 399 289    9/2004

OTHER PUBLICATIONS

R. Valentine et al., "Advances in Absorbable Biomaterials and Nasal Packing," 2009, Otolaryngologic Clinics of North America, vol. 42, pp. 813-828.
F. Virgin et al., "Evolving Materials and Techniques for Endoscopic Sinus Surgery," 2010, Otolaryngologic Clinics of North America, vol. 43, pp. 653-672.
V. Bugten et al., "Effects of Nonabsorbable Packing in Middle Meatus after Sinus Surgery," Jan. 2006, The Laryngoscope, vol. 116, pp. 83-88.
R. Chandra et al., "Advantages and disadvantages of topical packing in endoscopic sinus surgery," 2004, Current Opinion in Otolaryngology and Head and Neck Surgery, vol. 12, pp. 21-26.
S. Huggins, "Control of Hemorrhage in Otorhinolaryngologic Surgery with Oxidized Regenerated Cellulose," Jul. 1969, The Eye, Ear, Nose and Throat Monthly, vol. 48, pp. 45-49.
Chi-Kee Leslie Shaw et al., "Effect of packing on nasal mucosa of sheep," Jul. 2000, The Journal of Laryngology and Otology, vol. 114, pp. 506-509.
Marcelle von Schoenberg et al., "Nasal packing after routine nasal surgery—is it justified?" Oct. 1993, vol. 107, pp. 902-905.
R. K. Chandra et al., "Long-Term Effects of FloSeal™ Packing After Endoscopic Sinus Surgery," May-Jun. 2005, American Journal of Rhinology, vol. 19, No. 3, pp. 240-243.
R. K. Chandra et al., "The Effect of FloSeal on Mucosal Healing after Endoscopic Sinus Surgery: A Comparison with Thrombin-Soaked Gelatin Foam," Jan.-Feb. 2003, American Journal of Rhinology, vol. 17, No. 1, pp. 51-55.
S. Frenkiel et al., "Use of Hylan B Gel as a Wound Dressing after Endoscopic Sinus Surgery," Aug. 2002, The Journal of Otolaryngology, vol. 31, No. 1, pp. S41-S44.
P.D. Karkos et al., "Day-case endoscopic sinus surgery using dissolvable haemostatic nasal packs: a pilot study," 2007, European Archives of Oto-Rhino-Laryngology, vol. 264, pp. 1171-1174.
M. S. Maccabee et al., "Effects of Topically Applied Biomaterials on Paranasal Sinus Mucosal Healing," Jul.-Aug. 2003, American Journal of Rhinology, vol. 17, No. 4, pp. 203-207.
J. Pomerantz et al., "Platelet Gel for Endoscopic Sinus Surgery," 2005, Annals of Otology, Rhinology and Laryngology, vol. 114, No. 9, pp. 669-704.
B. A. Woodworth et al., "A gelatin-thrombin matrix for hemostasis after endoscopic sinus surgery," 2009, American Journal of Otolaryngology—Head and Neck Medicine and Surgery, vol. 30, pp. 49-53.
P. J. Wormald et al., "A prospective single-blind randomized controlled study of use of hyaluronic acid nasal packs in patients after endoscopic sinus surgery," Jan.-Feb. 2006, American Journal of Rhinology, vol. 20, No. 1, pp. 7-10.
M. Levi et al., "Two-Way Interactions Between Inflammation and Coagulation," 2005, TCM, vol. 15, No. 7, pp. 254-259.

(Continued)

*Primary Examiner* — Brandon Fetterolf
*Assistant Examiner* — Yih-Horng Shiao
(74) *Attorney, Agent, or Firm* — Jacobson Holman, PLLC.

(57) ABSTRACT

A surgical gel system for coating and adhering to a wound area to control bleeding while supporting wound healing comprises polyanhydroglucuronic acid or a biocompatible salt in an amount of from 1% to 15% by weight and pectin in an amount of in an amount of from 0.1% to 9% by weight. The gel system may be used for stopping bleeding during or after sinus surgery, for stopping bleeding in ear nose and throat procedures, for stopping bleeding in gynecological procedures, or for stopping bleeding in internal organ procedures.

20 Claims, 2 Drawing Sheets

(56) References Cited

OTHER PUBLICATIONS

M. Levi et al., "Bidirectional Relation Between Inflammation and Coagulation," 2004, American Heart Association: Circulation, pp. 2698-2704.

N. Hirsch et al., "The Evolution of Laparoscopic Surgery in Routine Health Care," 1995, International Journal of Technology Assessment in Health Care, vol. 11, No. 4, pp. 779-785.

J. E. Varela et al., "Outcomes of laparscopic and open colectomy at academic centers," 2008, The American Journal of Surgery, vol. 196, pp. 403-406.

A J Singer et al., "A Porcine Epistaxis Model: Hemostatic Effects of Octylcyanoacrylate," 2004, Otolaryngology—Head and Neck Surgery, vol. 130, pp. 553-557.

* cited by examiner

SURGICAL GEL SYSTEM

This is a national stage of PCT/IE11/000,029 filed Jun. 1, 2011 and published in English, claiming benefit of U.S. provisional application No. 61/344,167, filed Jun. 3, 2010, hereby incorporated by reference.

INTRODUCTION

Surgical access to a surgical field while there is any level of bleeding from the field can be significantly limited to the point that surgery must be discontinued until the bleeding is controlled. In some instances uncontrolled bleeding into and around a surgical field means that a particular type of surgery cannot be undertaken.

In general surgery, thermal cautery and suction have become the main methods of limiting the effects of bleeding from interfering with visibility and access to the surgical field. Although effective in controlling moderate levels of oozing bleeding, cautery results in increased incidence of scarring and adhesions. In the case of control of bleeding by thermal coagulation techniques (cautery) any temperature over 50° C. produces protein denaturation with resultant extensive thermal damage locally and at a distance from the applied temperature. This tissue damage is presented as fibrosis and scarring in the area of the denaturation. In procedures where cosmetic outcome is important or where delicate tissue is involved, less tissue injuring hemostatic techniques other than, or in combination with cautery should be considered. Such procedures include those of the ear, nose and throat (ENT), general reconstructive, neurological, vascular, oncological resection and gynecological.

In narrow passageway surgeries, such as endoscopic sinus surgery [1, 2], surgery is used to achieve sinus enlargement and to remove obstructing tissue and/or undesirable tissue growth. Removal of vascularized tissue from these passageways results in a moderate to robust degree of bleeding. Cautery use should be minimized for bleeding control because of the associated scarring. Hemostatic packing [3-7] composed of Vaseline soaked ribbon gauze, oxidized cellulose, gelatin, carboxymethyl cellulose or collagen are often used to control bleeding, however their placement occludes the passageway, temporarily disrupting the surgical procedure until their removal that can lead to postoperative bleeding. Hemostatic gel systems [8-15] are available; however they suffer from difficulties that are addressed by this invention disclosure. These difficulties can include insufficient hemostatic efficacy [11, 14], interference with access to and visualization of the surgical site [8, 9, 11, 14, 15], promotion of scarring [8, 9, 12-15] and/or concern with antibody formation and disease transmission in the case of biologic agents [8, 9, 12-14]. Some delivery formats of agents that provide effective haemostasis by strong direct interaction with the intrinsic clotting cascade have been found to cause adverse adhesions and scarring on wound healing [16, 17].

Often ENT, reconstructive, vascular and oncological surgeries are performed using laparoscopic and endoscopic procedures that are the principal elements of minimally invasive surgery (MIS) as well as of robotic and tele-monitoring surgery [18]. MIS dramatically reduces tissue destruction during the surgical procedure. There is decreased post-operative pain, faster recovery time, lower in-hospital morbidity rate, and improved cosmetic outcome [19]. The increased use of the minimal invasive techniques in surgical procedures not only improves patient outcomes but also saves significant health care costs annually.

There is a need to provide non-scarring, non-interfering control of bleeding during MIS for efficient and successful outcomes.

STATEMENTS OF INVENTION

According to the invention there is provided a gel system comprising polyanhydroglucuronic acid or a biocompatible salt thereof and pectin. The polyanhydroglucuronic acid or a biocompatible salt thereof is present in an amount of from 1% to 15% by weight. The pectin is present at concentrations in the range of 0.1% to 9% by weight of the gel system. The pectin may comprise approximately 3.6% or 4% by weight of the gel system. We have surprisingly found that this range is optimum to achieve gel flowability and tack for adhesion to tissue.

The polyanhydroglucuronic acid or a biocompatible salt thereof may be present in the range of 1% to 15% (w/w) to provide the optimum bleeding control for the particular intended use of the gel. Preferably the polyanhydroglucuronic acid or biocompatible salt thereof is present in the range of from 3% to 10% (w/w)

The gel system is readily administered to bleeding surgical fields to displace blood and to adhere to tissue to effectively control bleeding, to promote wound healing with reduced scarring, to allow visualization and access to the same surgical fields and can be removed subsequently without rebleeding by saline lavage.

The viscosity of the composition for use with nasal mucosa wounds and other surgical procedures is in the range of 100,000 to 350,000 cP when measured at 37° C. and preferably in the range of 200,000 to 300,000 cP or 200,000 to 350,000 cP. For such applications the polyanhydroglucuronic acid or biocompatible salt thereof is present in an amount of about 9% w/w.

The viscosity of the gel is measured using a Brookfield DVII-Pro Digital viscometer with Small Sample Adapter and an LV-4 spindle. Measurements are made at a low shear rate (0.3 RPM) at 37° C.

The tack of the gel is measured using EN-1719:1998 [Tack measurement for pressure-sensitive adhesives—Determination of loop tack] with a 1"×7" Teflon™ loop at 23±2° C. and a crosshead speed of 5 mm/s.

The tack of the gel when measured using EN-1719:1998 with a 1"×7" Teflon™ loop is most preferably between 70 mN and 110 mN.

The viscosity of the composition for use to treat bleeding on topical wounds is in the range of 25,000 to 200,000 cP when measured at 37° C. and preferably in the range of 75,000 to 125,000 cP. For such applications the polyanhydroglucuronic acid or biocompatible salt thereof is present in an amount of about 4% w/w.

In one embodiment the system comprises a lubricating agent such as glycerine

In one embodiment the gel system comprises a stability enhancer. The stability enhancer may be selected from one or more of ethanol and potassium sorbate.

In one aspect the gel system comprises glycerine in an amount from of 2% to 8% (w/w), ethanol in an amount of 0% to 8% (w/w) and potassium sorbate in an amount of from 0.05% to 1% (w/w).

In one aspect the gel system comprises approximately 9% (w/w) polyanhydroglucuronic acid, approximately 4% (w/w) pectin, approximately 3% (w/w), glycerine, approximately 5% (w/w) ethanol, approximately 0.2% (w/w) potassium sorbate, and approximately 78.8% (w/w) water.

In one aspect the gel system comprises approximately 9% (w/w) polyanhydroglucuronic acid, approximately 3.6% (w/w) pectin, approximately 2.9% (w/w), glycerine, approximately 5.1% (w/w) ethanol, approximately 0.2% (w/w) potassium sorbate, and approximately 79.2% (w/w) water These are particularly for nasal use.

In another aspect the gel system comprises approximately 4% (w/w) polyanhydroglucuronic acid, approximately 4% (w/w) pectin, approximately 4% (w/w), glycerine, approximately 5% (w/w) ethanol, approximately 0.5% (w/w) potassium sorbate, and approximately 82.5% (w/w) water. This is particularly to treat bleeding on topical wounds.

The invention also provides a topical composition comprising a gel system of the invention.

The invention further provides a delivery device having a gel system of the invention. The delivery device may be selected from a syringe, a tube, a spray bottle or a spray can.

The invention also provides the use of the gel system of the invention for stopping bleeding during or after sinus surgery.

The invention further provides the use of the gel system of the invention for stopping bleeding in ear nose and throat procedures.

The invention also provides the use of the gel system of the invention for stopping bleeding in gynecological procedures.

The invention further provides the use of the gel system of the invention for stopping bleeding in internal organ procedures.

The present invention provides a gel based system that controls bleeding during and after sinus surgery while supporting the wound healing process. In particular, the present invention provides preparations using polyanhydroglucuronic acid in combination with pectin that when applied controls bleeding by coating the surface of the injury allowing interaction between blood from the bleeding site and the microdispersed polyanhydroglucuronic acid which controls the bleeding.

The invention provides a system that coats the injured area and adheres, remaining on the bleeding site allowing the polyanhydroglucuronic acid to interact with components of the blood to accelerate the management of the bleeding.

The system viscosity is an important feature and it contains pectin as a viscosity modifier to help manage the viscosity of the final system formulation which is important for the function of the system. The system may also contain a glycerin base which aids in the feel, flow characteristics and general cohesion of the system.

We have found that the system successfully interacts with blood from an injury in a nasal wound and controls the bleeding quickly while maintaining the patency of the nasal cavity.

We have also found that the system in addition to controlling bleeding promotes the wound healing process and regeneration.

The system may also comprise one or more components selected from a group consisting of a preservative, a moisturizer, a surfactant, a thickener, an emulsifier and an adhesive.

The gel system may be used to reduce bleeding in other surgical processes or topical wounds.

The gel system of the invention is stable during storage and administration and can be applied directly to bleeding wounds in surgery, to displace the blood, and adhere to tissue to quickly control the bleeding without obscuring or interfering with access to the surgical site and can be removed subsequently without rebleeding by saline lavage. The gel system promotes healing and results in reduced incidence of scar formation.

The invention provides novel tissue wetting, bioadhesive compositions for controlling bleeding and for promoting healing with scar reduction without obscuring or Interfering with access to a surgical field The important features of the gel are that 1) it can be applied directly to bleeding fields, 2) it quickly wets and adheres to tissue rapidly, 3) it is haemostatic, 4) it is biocompatible, promotes wound-healing and reduces scarring 5) it can be applied quickly displacing blood and sealing injury, 6) it can be removed by suction, lavage or absorption without causing rebleeding, and 7) the gel can be administered so as to control bleeding without interfering with surgical field visualisation or access.

The invention further provides for tube directed delivery for topical, endoscopic or laparoscopic application to a bleeding surgical field. The tip of the tube may be conformed to provide optimal delivery of the gel to the surgical field. The tip configuration would allow provision of a ribbon profile, rectangular, circular, elliptical or any other to be delivered to the surgical site.

The invention also provides the use of the gel system of the invention for control of bleeding during or after sinus surgery.

The invention further provides the use of the gel system of the invention for control of bleeding in ear nose and throat procedures.

The invention further provides the use of the gel system of the invention for control of bleeding in reconstructive plastic surgery.

The invention further provides the use of the gel system of the invention for control of bleeding in vascular surgery.

The invention further provides the use of the gel system of the invention for control of bleeding in neurological surgery.

The invention further provides the use of the gel system of the invention for control bleeding in oncological resection surgery involving the biopsy and removal of tumors.

The invention also provides the use of the gel system of the invention for control of bleeding in gynecological surgery.

The present invention provides gel system on the invention that controls bleeding during and after surgery while supporting the wound healing process and without obscuring or interfering with the surgical field and thus allowing continued surgical access to the site. In particular, the present invention provides gel preparations of polyanhydroglucuronic acid in combination with pectin that when applied control bleeding by coating the surface of the injury allowing interaction between blood from the bleeding site and the polysaccharide which controls the bleeding.

The viscosity and tack of the gel are important functional elements for rapidly achieving haemostasis. The viscosity directly affects the cohesiveness of the gel and its ability to displace blood and remain intact at the bleeding surgical field, thus providing contact with the tissue beneath the blood. Too low a viscosity would mean the gel would disperse in the blood before contacting the tissue, while too high a viscosity would interfere with the ability of the gel to be delivered from the delivery device. The tack of the gel directly determines how well the gel will adhere to the tissue and hence how long it will be able to resist the direct flow of blood and provide opportunity for hemostasis. Pectin is used to manage the viscosity of the final system formulation that is important for the function of the system. The system may also contain a glycerin plasticizer that aids in the delivery characteristics of the gel without adversely affecting gel cohesion.

Control of bleeding in a swine injury model of sinus bleeding has demonstrated that the gel systems are highly effective at quickly controlling sinus bleeding while maintaining the patency of the nasal cavity.

Rat and swine wound healing studies have also demonstrated that the systems in addition to controlling bleeding also promote the wound healing process and regeneration.

To test that the gel systems are stable at room temperature for at least 12 months, accelerated aging testing at 42° C. equivalent to 12 months at 25° C. was performed in the case of gamma-irradiated polyanhydroglucuronate gel.

The gel may be used to stop bleeding in ear nose and throat procedures as well as surgical procedures such as neurological, vascular, general reconstructive, oncological and gynecological procedures as well as topical uses of the composition.

BRIEF DESCRIPTION OF THE DRAWINGS

The invention will be more clearly understood from the following description of an embodiment thereof, given by way of example only, with reference to the accompanying drawings, in which.

DETAILED DESCRIPTION

Although the disclosure hereof is detailed and exact to enable those skilled in the art to practice the invention, the physical embodiments herein disclosed merely exemplify the invention which may be embodied in other ways. While the preferred embodiment has been described, the details may be changed without departing from the invention.

The present invention provides products and methods for controlling the bleeding from wounds such as those occurring during surgery without affecting access or visualisation of the surgical site. Upon application of the gel system to the bleeding surgical site, the gel system adheres to and coats the immediate injury providing for the polysaccharide to both restrict and interact with blood flowing from injury. This interaction reduces the bleeding from the site by physical occlusion and by accelerating the hemostasis of the blood.

Most notably, the system of the present invention has shown beneficial qualities by successfully reducing bleeding quickly thus enabling the surgeon to continue the required procedure. Further notably the system stops the bleeding in a manner that allows continuation of the surgical procedure as the system functions without occluding the view of the surgical field. In demonstration of the applicability of this system to the general surgical field, this invention disclosure has chosen as its model the difficult surgical field of endoscopic sinus surgery within the nasal passage.

The present system provides advantages over other nasal hemostatic treatments not alone in its speed to controlling bleeding for the surgeon but also in the lack of pain and discomfort experienced in use by the patient associated with other methods that employ packing or stent systems. A further advantage of this system is the support of the wound healing process by the gel system that is in contrast to other nasal bleeding treatments that can have unfavourable consequences on the wound healing process.

The system described herein may be applied to the injured sites in many different types of delivery device such as syringes, tubes or other such commonly used gel delivery devices.

Having described the invention in general terms, reference is now made to specific non-limiting examples.

Polyanhydroglucuronic Acid Preparation

In this example, the raw material for preparing a calcium sodium salt of microdispersed polyanhydroglucuronic acid were cotton linters containing 99.1% w/w of α-cellulose and oxidized in 60% w/w nitric acid with an admixture of 3.8% nitrous acid at a temperature of 30° C. max in analogy to procedure of GBP 709684. The resulting product contained:

| | |
|---|---|
| carboxyl groups | 16.3% w/w |
| carbonyl groups | 3.1% w/w |
| bound nitrogen less than | 0.5% |

600 ml of water and 27 g of sodium hydroxide were transferred to a 2000 ml jacketed glass-vessel stirred by Ultra-Turrax stirrer T50 (IKA Werke CmbH & Co. KG, Germany). After dissolving of the sodium hydroxide the above defined oxidized cotton linters containing about 10% of volatile matter were added while constantly stirring at ca 4000 rpm for at least 30 minutes. Temperature was maintained on 30° C. max. Then 80 grams of water solution of calcium chlorate hexahydrate (1/1 w/w) and 25 g of peroxide were added and reaction mixture was stirred at 5000 rpm for next 60 minutes at temperature of 30° C. max. 1000 ml of 93% ethanol were added stepwise during about 10 minutes and the resulting colloid dispersion solution was then filtered. Obtained filter cake was dispersed into 55% water-ethanol mixture and another filtration of the residue was redispersed into 500 ml isopropanol and allowed to stand for at least 5 hours. All these steps were in analogy to application WO 2007/026341. Isolated filter cake was again redispergated into 500 ml isopropanol and to the reaction mixture there was added 5 grams of carboxymethyl cellulose, blanose 12M31P (Aqualon Hercules; Wilmington, Del., U.S.A). Mixture was allowed to stand for at least 10 hours. Final prepared mixture was filtered and dried in a vacuum drier at the temperature of 70° C. and milled.

An analysis of the product obtained yielded:

| | |
|---|---|
| loss on drying | 2.3% w/w |
| carboxyl group content | 16.5% w/w |
| bound nitrogen | 0.1% w/w |
| calcium content | 5.1% w/w |
| sodium content | 3.7% w/w |
| specific surface area | 82 $m^2 \cdot g^{-1}$ |

Example 1

Sterile Haemostatic Gel

A gel was prepared with the following composition.

| Ingredients | Formulation (% (w/w) final formulation) |
|---|---|
| Calcium-sodium polyanhydroglucuronic acid | 9 |

-continued

| Ingredients | Formulation (% (w/w) final formulation) |
|---|---|
| Pectin | 4 |
| Potassium sorbate | 0.2 |
| Gylcerin | 3 |
| $dH_2O$ | 78.8 |
| Ethanol | 5 |

The viscosity of the prepared gel was 617,000 cP at 37 degrees C. (Brookfield DV-II+ PRO Digital Viscometer, LV-4 spindle, 0.3 RPM).

The gel is sterilised by gamma irradiation between 4 and 45 kGy, sufficient to produce a sterility assurance limit (SAL) of $10^{-6}$. Alternatively, material may be processed aseptically from materials to produce a material with a sterility assurance limit (SAL) of $10^{-6}$.

The viscosity of the sterilised gel was 311,000 cP at 37 degrees C. (Brookfield DVII+ PRO Digital Viscometer, LV-4 spindle, 0.3 RPM)

The viscosity of the material is suitable for dispensing through a nozzle or small office to the site of bleeding. The dispensing apparatus could be a syringe, a tube or any such similar device. In this example the gel was loaded into a syringe prior to sterilsation. After opening of the syringe tip at point of use a flexible/malleable tip may be attached to the tip to facilitate insertion into a sinus cavity.

Example 2

Sterile Haemostatic Gel

A gel was prepared with the following composition.

| Ingredients | Formulation (% (w/w) final formulation) |
|---|---|
| Calcium-sodium polyanhydroglucuronic acid | 9.0 |
| Pectin | 3.6 |
| Potassium sorbate | 0.2 |
| Gylcerol | 2.9 |
| Deionised $H_2O$ | 79.2 |
| Ethanol | 5.1 |

The viscosity of the prepared gel was 607,000 cP at 37 degrees C. (Brookfield DV-II+ PRO Digital Viscometer, LV-4 spindle, 0.3 RPM).

The gel is sterilized by gamma irradiation between 4 and 45 kGy, sufficient to produce a sterility assurance limit (SAL) of $10^{-6}$. Alternatively, material may be processed aseptically from materials to produce a material with a sterility assurance limit (SAL) of $10^{-6}$.

The viscosity of the sterilised gel was 250,000 cP at 37 degrees C. (Brookfield DVII+ PRO Digital Viscometer, LV-4 spindle, 0.3 RPM)

The viscosity of the material is suitable for dispensing through a nozzle or small orfice to the site of bleeding. The dispensing apparatus could be a syringe, a tube or any such similar device. In this example the gel was loaded into a syringe prior to sterilsation. After opening of the syringe tip at point of use a flexible/malleable tip may be attached to the tip to facilitate insertion into a sinus cavity.

The tack of the gel was measured using EN-1719:1998 [Tack measurement for pressure-sensitive adhesives—Determination of loop tack] with a 1"×7" Teflon™ loop at 23±2° C. and a crosshead speed of 5 mm/s.

Three batch lots of the gel were tested as follows as per EN-1719:1998. The results of the Tack test are given in FIG. 1 with the ranges presented below.

Figure 1:
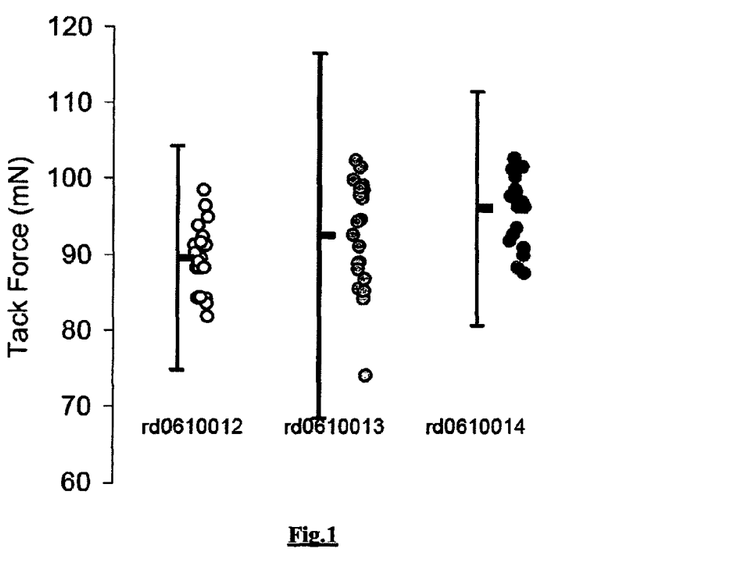
FIG. 1 shows the results of tack tests on gels according to the invention.

| Lot Specification | Tack Force (mN) |
|---|---|
| rd0610012 | 82-99 |
| rd0610013 | 74-99 |
| rd0610014 | 91-103 |

Example 3

Use of Sterile Haemostatic Gel in Swine Nasal Mucosal Laceration Injuries

Figure 2:
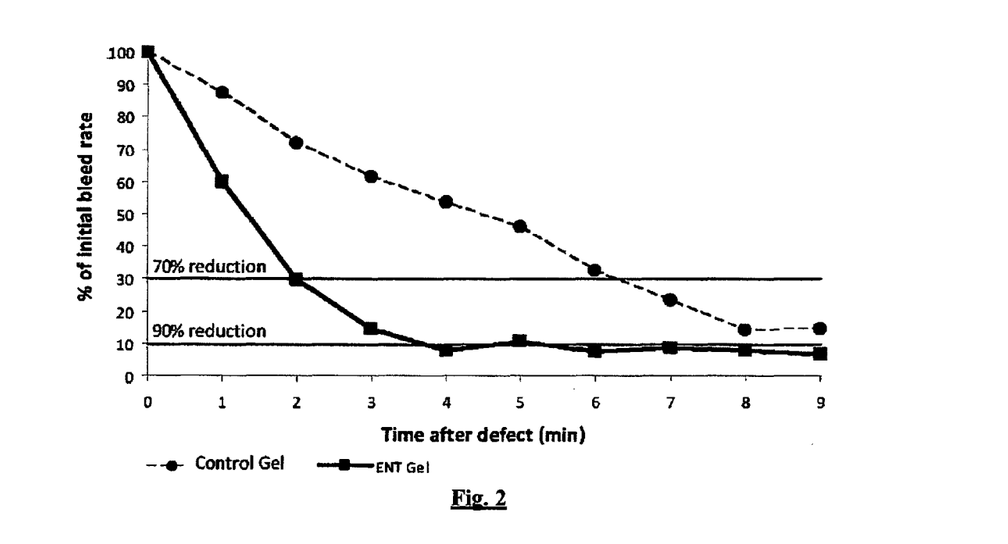
FIG. 2 is a graph of the residual bleeding rate from time of application of control or test gel system in a swine model of endopscopic surgical sinus bleeding.

The haemostatic gel of example 1 was applied to swine nasal mucosa laceration injuries with bleeding rates between 3 to 25 mL/min and successful hemostasis was achieved. A commercially available nasal dressing and sinus stent hydrogel composed of cross-linked hyaluronic acid was used as a control gel. Application of the calcium-sodium microdispersed polyanhydroglucuronic acid containing gel coated the surface of the injury, facilitates interaction between the bleeding site and the microdispersed oxidized cellulose (FIG. 2). 70% reduction in bleeding was achieved within 1.5 minutes and with 90% reduction in bleeding in as little as 3 minutes. The gel was adherent and coated vertical and inverted tissue surfaces. The control gel only achieved 70% reduction in bleeding after approximately 6 minutes and did not achieve 90% reduction in bleeding in the course of the study. This swine study demonstrated successfully the efficacy of the formulation to stop bleeding in a nasal injury such as that seen in sinus surgeries especially when compared to a commercially available gel for similar use.

Example 4

Efficacy and Histological Evaluation of Sterile Gel

A frequent complication of functional endoscopic sinus surgery (FESS) is the development of post-operative adhesions, which may block normal mucociliary drainage pathways of the sinuses. This blockage can cause a recurrence of sinusitis and require subsequent surgical procedures. To prevent post-operative bleeding and adhesion formation, nasal packing is often used. Alternatives to nasal packing include intranasal splints and gels, though the majority of these products employ the tamponade effect to achieve haemostasis, which can contribute to abnormal nasal breathing and significant patient discomfort. An optimal haemostat for endoscopic sinus surgery would effectively control bleeding and minimise adhesion formation, scar formation and inflammation of the mucosal tissue. The purpose of this study was to evaluate the post-operative performance of the haemostatic gel.

Materials and Methods:

Singer et al [20] describes a porcine model to mimic functional and morphological changes in mucosa following FESS. Mucosal stripping of the lateral nasal wall induced bleed rates characteristic of FESS in 10 Yorkshire pigs and the haemostatic gel of Example 2 was applied to control bleeding. Defect sites (n=10) were treated and allowed to heal for 2 weeks. At euthanasia, each site was qualitatively assessed for scarring, clot formation, nasal cavity patency and residual hemostatic material. Histological sections were taken from each defect site, stained with Hematoxylin and Eosin (H&E) and blindly evaluated by an independent pathologist to assess cell morphology, mucosal re-epithelialization and granulation tissue.

Figure 3:
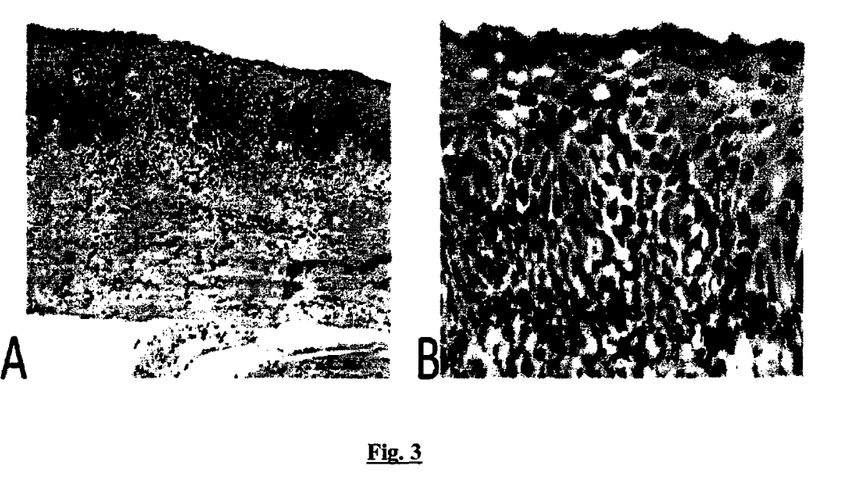
FIG. 3 is a representative histological appearance (H&E stain) at day 14 depicting re-epithelialization of defect with no granuloma formation (A—10×, B—40×)

Results:

All animals tolerated the surgeries well and returned to normal activity immediately. Intra-operative assessment showed that bleeding was effectively controlled at all defect sites in an average of 3.1 minutes following application of the haemostatic gel of example 2. Endoscopic evaluation at necropsy indicated no evidence of adhesions, scarring or residual hemostatic material. No clots or signs of recent bleeding were observed and no gross inflammation or erythema was noted in any defect. Histological evaluation showed excellent re-epithelization of all defect sites with no cellular abnormalities (FIG. 3). No foreign material or granuloma formation was identified in any specimen. Quality of the underlying tissue was shown to be in a "healing" phase suggestive of a response to the mucosal stripping injury. A small amount of epithelial scarring was present in the normal range for this stage of healing, but no hypertrophic scarring was observed.

Conclusion:

The investigation demonstrates that the haemostatic gel of the invention can effectively control bleeding associated with FESS. Furthermore, the gel enables re-epithelialisation of the mucosa and subsequent natural wound healing without adhesion or granuloma formation.

Example 5

Clinical Evaluation—Sterile Haemostatic Gel

The purpose of the post-market clinical evaluation was to summarise the clinical use to-date of the haemostatic gel. Specifically, the objectives of the clinical evaluation were to evaluate the gel's intra-operative haemostatic efficacy, its ability to coat the mucosal surface, delivery device ergonomics and various elements of the gel's application technique.

The haemostatic gel of example 2 was utilised by five surgeons in nine separate cases. The nine cases can be broken down as follows: five functional endoscopic sinus surgeries (FESS), two FESS procedures combined with septoplasty and two FESS procedures combined with sub-mucosal resection (SMR) of the inferior turbinate.

Surgeon reaction to the haemostatic gel was uniformly positive and the summarised responses to the individual questions are tabulated in the Table below. Surgeons appreciated the flexible applicator tip supplied with the gel that allowed surface application of the gel throughout the sinus cavities. Moreover, all surgeons indicated that application of the product controlled observed bleeding to their satisfaction. Traditional products used to impart haemostasis depend upon a tamponade effect, whereby the pressure applied by volume-filling gel helps to control bleeding; however, the haemostatic gel was able to control bleeding at the mucosal surface while keeping the nasal passages open. In summary, the device of the invention successfully controlled minimal-moderate bleeding typically associated with ENT surgical procedures.

Data has also been collected from patient follow-up visits to evaluate tissue healing characteristics, incidence of post-operative bleeding and nasal patency. These results serve as confirmatory data of the product's ability to minimise oedema and prevent adhesions post-operatively. The follow-up data indicates that the gel cleared from the patient following surgery with no adverse tissue reactions

TABLE

Clinical Evaluation Questionnaire Results

| Question | # of Responses |
|---|---|
| 1) Procedure performed | |
| FESS only | 5 |
| FESS with septoplasty | 2 |
| FESS with SMR | 2 |
| 2) Observed bleeding | |
| Trace | 0 |
| Minimal | 4 |
| Moderate | 5 |
| Severe | 0 |
| 3) Application of gel | |
| During procedure only | 1 |
| At end of procedure only | 2 |
| Both during and at end of procedure | 6 |
| 4) Was applicator tip sufficient for use? | |
| Yes | 9 |
| No | 0 |
| 5) Did gel easily coat mucosal surface? | |
| Yes | 9 |
| No | 0 |
| 6) Did product control bleeding? | |
| Yes | 9 |
| No | 0 |
| 7) Was amount of gel supplied sufficient? | |
| Yes | 9 |
| No | 0 |
| 8) Was IFU sufficient for use? | |
| Yes | 9 |
| No | 0 |

The haemostatic gel of the invention effectively coats the mucosal tissue while simultaneously controlling bleeding typically associated with ENT surgical procedures.

Example 5

Non Sterile Haemostatic Gel

A gel was prepared with the following composition.

| Ingredients | Formulation (% (w/w) final formulation) |
|---|---|
| Calcium-sodium polyanhydroglucuronic acid | 4 |
| Pectin | 4 |
| Potassium sorbate | 0.5 |
| Gylcerin | 4 |
| dH2O | 82.5 |
| Ethanol | 5 |

The prepared gel had a viscosity of cP at 37 degrees C. (Brookfield DV-II+ PRO Digital Viscometer, LV-4 spindle, 0.3 RPM).

Example 6

Non Sterile Gel—Stop Bleeding

The gel of example 5 was filled into 15 ml tube dispensers and was not sterilized. The gel was applied to a bleeding grazed hand wound by application from the tube. Gentle spreading of the gel over the bleeding wound stopped the bleeding from the wound in 2 minutes.

Example 7

Non Sterile Gel Wound Healing

The Gel prepared in Example 5 was tested for its ability to support wound healing. A rat excisional model (BioPharm, Study Code: 179/2006 Efficiency of the Test Items on Dermal Wound Healing in Rats) was used to examine the potential wound healing effects of the haemostatic gel. The rats underwent experimental wounding on dorsal region of the animal. Experimental wounds were made under general ketamine and xylazine anaesthesia (ketamine 100 mg/kg+xylazine 10 mg/kg of body weight). The anaesthetic agents were administered intraperitoneally into abdominal region. An appropriate sized shaved area was created on the rats back region and 3 wounds (1 cm diameter) were made with a steel punch appliance on this area. All animal work was performed under local guidelines and regulations and to GLP standard.

The gel of example 5 (or a non treatment control) was topically administered twice a day on the wounds with sufficient gel applied to cover the exposed wound. The wound area reduction, closure and healing (incidence of wound secretion, haemorrhagic crust and scar formations) were monitored daily. At the end of healing process all rats were sacrificed by $CO_2$ inhalation and dermal samples were taken for histological examination.

Figure 4:
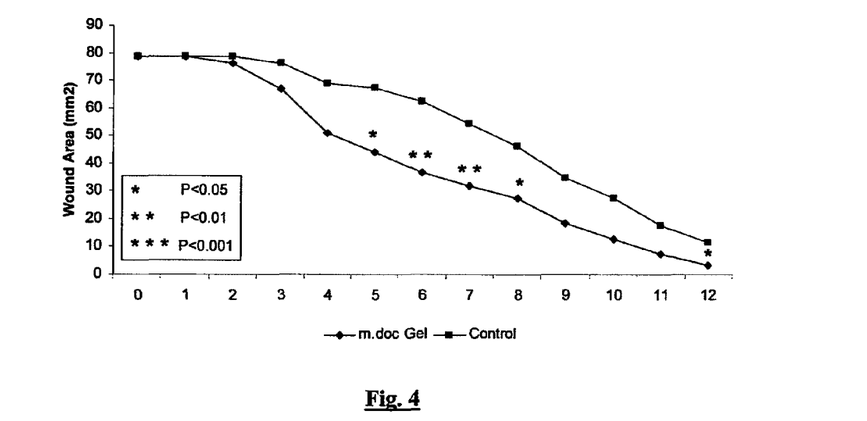
FIG. 4 is a graph of mean wound area (n=6) for both the control and the m.doc gel groups following twice daily application of the gel of the invention over 12 days. Statistical significance between the groups was considered significant at $p<0.05$.

The wound area was measured for each wound daily and the results for the untreated control and the gel can be seen in FIG. 4.

The results found showed significantly improved dermal healing from day 5 through day 8. Subsequently by the end of the study the control group had also shown reduction in wound area. It can be concluded from these results that the gel did have a stimulatory effect on wound healing process and was certainly quicker to achieve wound closure of the experimental injuries.

Example 7

Antimicrobial Gel

The Gel prepared in Example 5 was tested for its ability to be antimicrobial. The antimicrobial efficacy of the gel was tested against a number of strains of micro-organisms consisting of bacteria, fungi and yeast. In summary, strains of micro-organisms were inoculated into tested preparations with storage of the inoculated preparations at the prescribed temperature, and sampling at determined time intervals and testing for viable counts of colony forming units (cfu) by US Pharmacopeia method 28. The decrease in cfus was measured and the results re presented in the Table below. It could be seen that the gel formulation was antimicrobial as it did reduce the numbers of microorganisms tested.

| Microorganism | Decrease of cfu number/24 hour |
| --- | --- |
| Pseudomonas aeruginosa CCM 1961 | >3 log |
| Staphylococcus aureus CCM 4516 | >3 log |
| Candida albicans CCM 8215 | >2 log |
| Aspergillus niger CCM 8222 | >2 log |

The prepared mixture can be used successfully as a haemostatic agent for a surgical gel intended to reduce bleeding.

Modifications and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

The invention is not limited to the embodiments hereinbefore described which may be varied in detail.

REFERENCES

1. Valentine, R., P. J. Wormald, and R. Sindwani, *Advances in absorbable biomaterials and nasal packing.* Otolaryngol Clin North Am, 2009. 42(5): p. 813-28, ix.
2. Virgin, F. W., B. S. Bleier, and B. A. Woodworth, *Evolving materials and techniques for endoscopic sinus surgery.* Otolaryngol Clin North Am, 2010. 43(3): p. 653-72, xi.
3. Bugten, V., et al., *Effects of nonabsorbable packing in middle meatus after sinus surgery.* Laryngoscope, 2006. 116(1): p. 83-8.
4. Chandra, R. K. and R. C. Kern, *Advantages and disadvantages of topical packing in endoscopic sinus surgery.* Curr Opin Otolaryngol Head Neck Surg, 2004. 12(1): p. 21-6.
5. Huggins, S., *Control of hemorrhage in otorhinolaryngologic surgery with oxidized regenerated cellulose.* Eye Ear Nose Throat Mon, 1969. 48(7): p. 420-3.
6. Shaw, C. L., et al., *Effect of packing on nasal mucosa of sheep.* J Laryngol Otol, 2000. 114(7): p. 506-9.
7. von Schoenberg, M., P. Robinson, and R. Ryan, *Nasal packing after routine nasal surgery—is it justified?* J Laryngol Otol, 1993. 107(10): p. 902-5.
8. Chandra, R. K., et al., *Long-term effects of FloSeal packing after endoscopic sinus surgery.* Am J Rhinol, 2005. 19(3): p. 240-3.
9. Chandra, R. K., D. B. Conley, and R. C. Kern, *The effect of FloSeal on mucosal healing after endoscopic sinus surgery: a comparison with thrombin-soaked gelatin foam.* Am J Rhinol, 2003. 17(1): p. 51-5.
10. Frenkiel, S., M. Y. Desrosiers, and D. Nachtigal, *Use of hylan B gel as a wound dressing after endoscopic sinus surgery.* J Otolaryngol, 2002. 31 Suppl 1: p. S41-4.
11. Karkos, P. D., et al., *Day-case endoscopic sinus surgery using dissolvable haemostatic nasal packs: a pilot study.* Eur Arch Otorhinolaryngol, 2007. 264(10): p. 1171-4.
12. Maccabee, M. S., D. R. Trune, and P. H. Hwang, *Effects of topically applied biomaterials on paranasal sinus mucosal healing.* Am J Rhinol, 2003. 17(4): p. 203-7.
13. Pomerantz, J. and J. M. Dutton, *Platelet gel for endoscopic sinus surgery.* Ann Otol Rhinol Laryngol, 2005. 114(9): p. 699-704.
14. Woodworth, B. A., et al., *A gelatin-thrombin matrix for hemostasis after endoscopic sinus surgery.* Am J Otolaryngol, 2009. 30(1): p. 49-53.
15. Wormald, P. J., et al., *A prospective single-blind randomized controlled study of use of hyaluronic acid nasal packs in patients after endoscopic sinus surgery.* Am J Rhinol, 2006. 20(1): p. 7-10.
16. Levi, M. and T. van der Poll, *Two-way interactions between inflammation and coagulation.* Trends Cardiovasc Med, 2005. 15(7): p. 254-9.
17. Levi, M., T. van der Poll, and H. R. Buller, *Bidirectional relation between inflammation and coagulation.* Circulation, 2004. 109(22): p. 2698-704.
18. Hirsch, N. and D. Hailey, *The evolution of laparoscopic surgery in routine health care.* Int J Technol Assess Health Care, 1995. 11(4): p. 779-85.

19. Varela, J. E., et al., *Outcomes of laparoscopic and open colectomy at academic centers*. Am J Surg, 2008. 196(3): p. 403-6.
20. Singer A J, McClain S A and Katz A. [A porcine epistaxis model: hemostatic effects of octylcyanoarylate. Otolaryngol Head Neck Surg, 2004; 130(5): 553-557.]

The invention claimed is:

1. A sterile gel for coating and adhering to a wound area to control bleeding whilst supporting wound healing, the gel comprising polyanhydroglucuronic acid or a biocompatible salt thereof in an amount of from 1% to 15% by weight and pectin in an amount of from 0.1% to 9% by weight, a stability enhancer, a lubricating agent and an antimicrobial agent, wherein a viscosity of the gel is from 100,000 to 350,000 cP when measured at 37° C., wherein a tack of the gel is from 70 mN to 100 mN, and wherein the stability enhancer is selected from the group consisting of one or more of ethanol and potassium sorbate.

2. The gel as claimed in claim 1 wherein the polyanhydroglucuronic acid or the biocompatible salt thereof is in an amount of from 3% to 10% by weight.

3. The gel as claimed in claim 1 wherein the comprising polyanhydroglucuronic acid or the biocompatible salt thereof is in an amount of approximately 9% by weight.

4. The gel as claimed in claim 1 wherein the pectin is in an amount of approximately 4%.

5. The gel as claimed in claim 1 wherein the pectin is in an amount of approximately 3.6%.

6. The gel as claimed in claim 1 wherein the viscosity of the gel is from 200,000 to 350,000 cP when measured at 37° C.

7. The gel as claimed in claim 1 wherein the viscosity of the gel is from 200,000 to 300,000 cP when measured at 37° C.

8. The gel as claimed in claim 1 wherein the lubricating agent comprises glycerine.

9. The gel as claimed in claim 8 wherein the glycerine is in an amount from of from 2% to 8% (w/w).

10. The gel as claimed in claim 1 wherein the stability enhancer comprises ethanol in an amount of from 0% to 8% (w/w).

11. The gel in claim 10 wherein the ethanol is present in an amount of from 3% to 7% (w/w).

12. The gel as claimed in claim 1 wherein the stability enhancer is potassium sorbate in an amount of from 0.05% to 1% (w/w).

13. The gel as claimed in claim 1 comprising glycerine in an amount of from 2% to 8% (w/w), ethanol in an amount of 0% to 8% (w/w) and potassium sorbate in an amount of from 0.05% to 1% (w/w).

14. A sterile gel comprising approximately 9% (w/w) polyanhydroglucuronic acid, approximately 4% (w/w) pectin, approximately 3% (w/w), glycerine, approximately 5% (w/w) ethanol, approximately 0.2% (w/w) potassium sorbate, and approximately 78.8% (w/w) water.

15. A sterile gel comprising approximately 9% (w/w) polyanhydroglucuronic acid, approximately 3.6% (w/w) pectin, approximately 2.9% (w/w) glycerine, approximately 5.1% (w/w) ethanol, approximately 0.2% (w/w) potassium sorbate, and approximately 79.2% (w/w) water.

16. The gel as claimed in claim 1 which is sterilisable by gamma irradiation.

17. The gel as claimed in claim 1 which is capable of being removed by dissolution, by surgical flushing (lavage) or by bioresorption or by biabsorption or by biodegradation.

18. The gel system as claimed in claim 1 which is capable of being applied to complex body geometries.

19. A syringe containing the gel as claimed in claim 1.

20. A method comprising the step of applying the gel as claimed in claim 1 to a wound to
control bleeding during or after sinus surgery;
control bleeding in ear nose and throat procedures;
control bleeding in general reconstructive plastic surgery;
control bleeding in neurological surgery;
control bleeding following biopsy;
control bleeding in vascular surgery;
control bleeding in oncological organ resection to remove tumors;
control bleeding in gynecological procedures; or
have a general topical control of bleeding.

* * * * *